(12) United States Patent
Evans et al.

(10) Patent No.: US 6,357,470 B1
(45) Date of Patent: Mar. 19, 2002

(54) VESSEL AND PIPELINE INSERTION TOOL

(75) Inventors: Willie V. Evans; Gary K. Evans, both of Kilgore, TX (US)

(73) Assignee: Accurate Tool Company, Kilgore, TX (US)

( * ) Notice: Subject to any disclaimer, the term of this patent is extended or adjusted under 35 U.S.C. 154(b) by 0 days.

(21) Appl. No.: 09/589,906

(22) Filed: Jun. 7, 2000

(51) Int. Cl.[7] .................. G01N 17/04; G01D 21/00; B23P 19/04
(52) U.S. Cl. .................. 137/317; 29/256; 29/263; 73/866.5; 137/315.01; 422/53; 251/214; 251/368
(58) Field of Search ............. 73/866.5, 863.81, 73/863.86, 86; 137/312, 317, 318, 315.01; 251/214, 368; 29/256, 263; 422/53; 436/3, 6

(56) References Cited

U.S. PATENT DOCUMENTS

| | | | | |
|---|---|---|---|---|
| 3,679,169 A | * | 7/1972 | Bedo et al. ............... | 251/214 |
| 3,857,410 A | * | 12/1974 | Bedo et al. ............... | 251/214 |
| 3,983,756 A | * | 10/1976 | Danguillier et al. ....... | 73/866.5 |
| 4,096,754 A | * | 6/1978 | Beveridge, Jr. et al. ... | 73/866.5 |
| 4,114,851 A | * | 9/1978 | Shivak et al. .............. | 251/214 |
| 4,120,313 A | * | 10/1978 | Lewis ........................ | 137/268 |
| 4,697,465 A | * | 10/1987 | Evans et al. ............... | 73/866.5 |
| 5,138,755 A | * | 8/1992 | Evans et al. ............... | 29/263 |
| 5,174,325 A | * | 12/1992 | Okel et al. .................. | 137/317 |
| 5,936,168 A | * | 8/1999 | Welker ....................... | 73/866.5 |
| 5,996,430 A | * | 12/1999 | Bellis, Sr. .................. | 73/866.5 |
| 6,068,018 A | * | 5/2000 | Robert ....................... | 251/368 |
| 6,085,777 A | * | 7/2000 | Welker ....................... | 137/317 |

\* cited by examiner

Primary Examiner—George L. Walton
(74) Attorney, Agent, or Firm—The Matthews Firm; William P. Ramey, III

(57) ABSTRACT

A packer joint is provided for mounting on a vessel or pipeline entry valve which includes a stinger guide and seal. Clamping collet are mounted within the packer to retain the stinger in the desired position. Different metals within the guide body from those of the stinger rod prevent gaulding and damage. A lock-up the rod may be released via a bore hole providing tapping access to the collets.

24 Claims, 6 Drawing Sheets

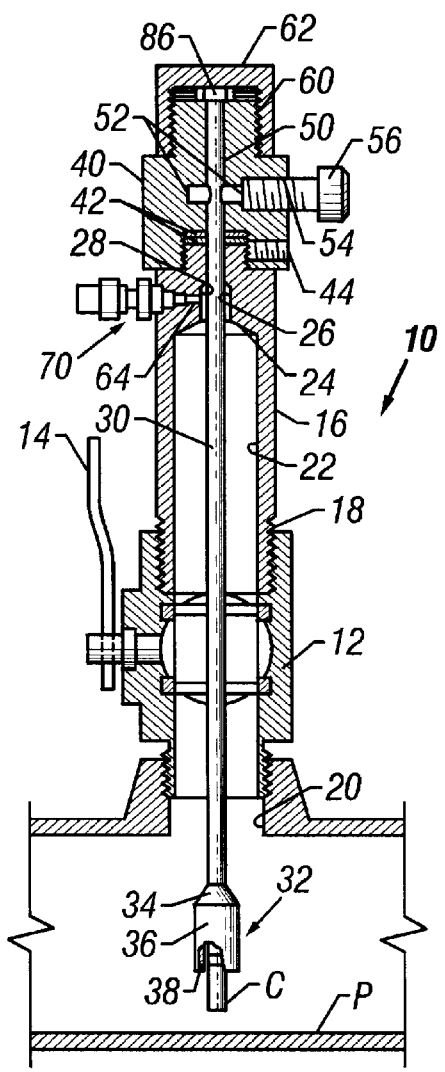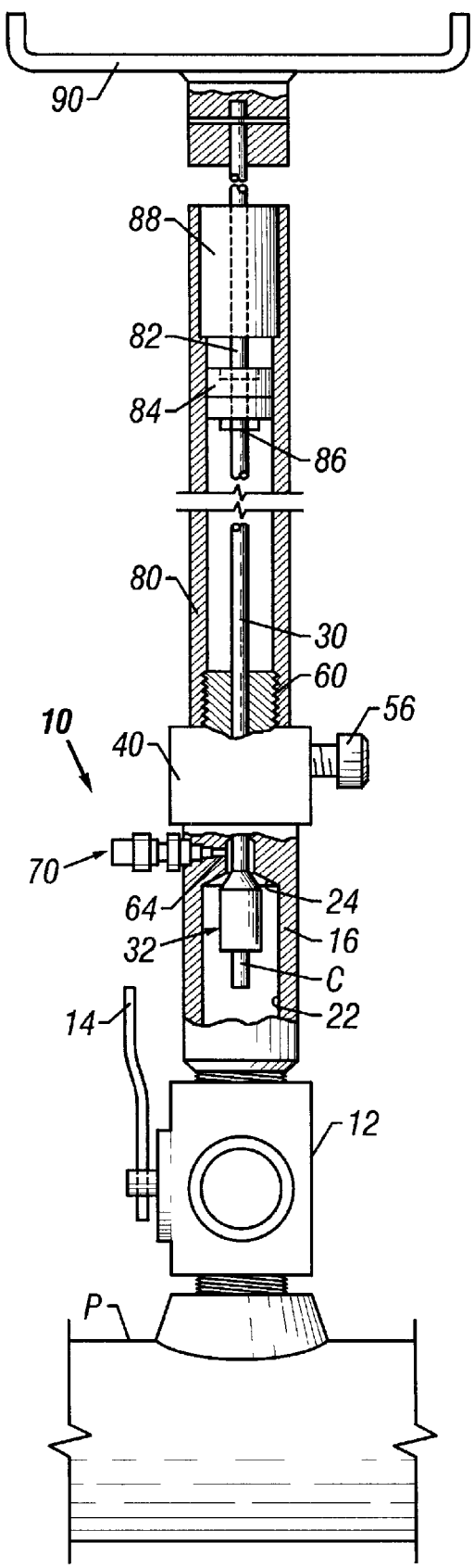
FIG. 1
FIG. 2

VESSEL AND PIPELINE INSERTION TOOL

FIELD OF THE INVENTION

The present invention relates generally to insertion tools and more particularly to a new and improved method and apparatus for the insertion of tools, test coupons and the like into vessels and pipelines, and for such other structures and methods as may be herein disclosed.

BACKGROUND OF THE INVENTION

Tools and other special devices are often required to be inserted into pressurized vessels and pipelines. One such device has been disclosed in our earlier U. S. Pat. No. 5,138,755. Such devices include corrosion coupon holders as disclosed in our earlier U.S. Pat. No. 4,697,465. Each of these prior patents is hereby incorporated by reference. Other devices include sample holders, probes, and fluid injection devices. Some of the devices come with self contained valves and packers to allow the device, sometimes called a stinger, to be inserted into the vessel or pipeline while sealing the pressure contained therein. If the pressure is significant, such as several hundred to several thousand pounds per square inch, it is often difficult to force the stringer into the vessel or pipeline against the pressure. In some instances gaulding and compression freeze up or lock up of the rod in the bore may still occur. It is to these problems and their solution that we have most recently turned our attention.

BRIEF DESCRIPTION OF THE DRAWINGS

The above mentioned and other objects and advantages of the present invention, and a better understanding of the principles and details of the present invention, will be evident from the following description taken in conjunction with the appended drawings.

The drawings constitute a part of this specification and include exemplary embodiments of the present invention, which may be embodied in various forms. It is to be understood that in some instances, various aspects of the invention may be shown exaggerated, reduced or enlarged, or otherwise distorted to facilitate an understanding of the present invention.

In the drawings appended hereto:

FIG. 1 is a sectional view of a test coupon holder associated with a pipe entry valve and a segment of pipeline, the test coupon being in position within the pipeline.

FIG. 2 is a partial sectional view showing a coupon withdrawn into the coupon holder housing.

FIG. 3 is a side elevational view of one embodiment employing the present invention mounted on a pipeline valve.

FIG. 4 is a side elevational view in cross section of one embodiment of the packer joint and mounting base employing the present invention.

FIG. 5 is a top view of one embodiment of the collet clamp as used in the packer joint of FIG. 4.

FIG. 6 is a top view of the collet of FIG. 5 clamped about a tubing stinger.

FIG. 7 is a side view of the collet clamp of FIG. 5 and FIG. 6.

FIG. 8 is a sectional view of a test coupon holder of the present invention associated with a pipe entry valve and a segment of pipe line, the test coupon being in position within the pipeline and the improvements of the present invention being shown in context.

FIG. 9 is a partial sectional view showing the coupon withdrawn into the coupon holder housing showing the present invention in context.

FIG. 10 is a cross sectional view of the body and the improvement of the present invention.

FIG. 11 is a cross sectional view of the body and the improvement of the present invention.

Figure 3:
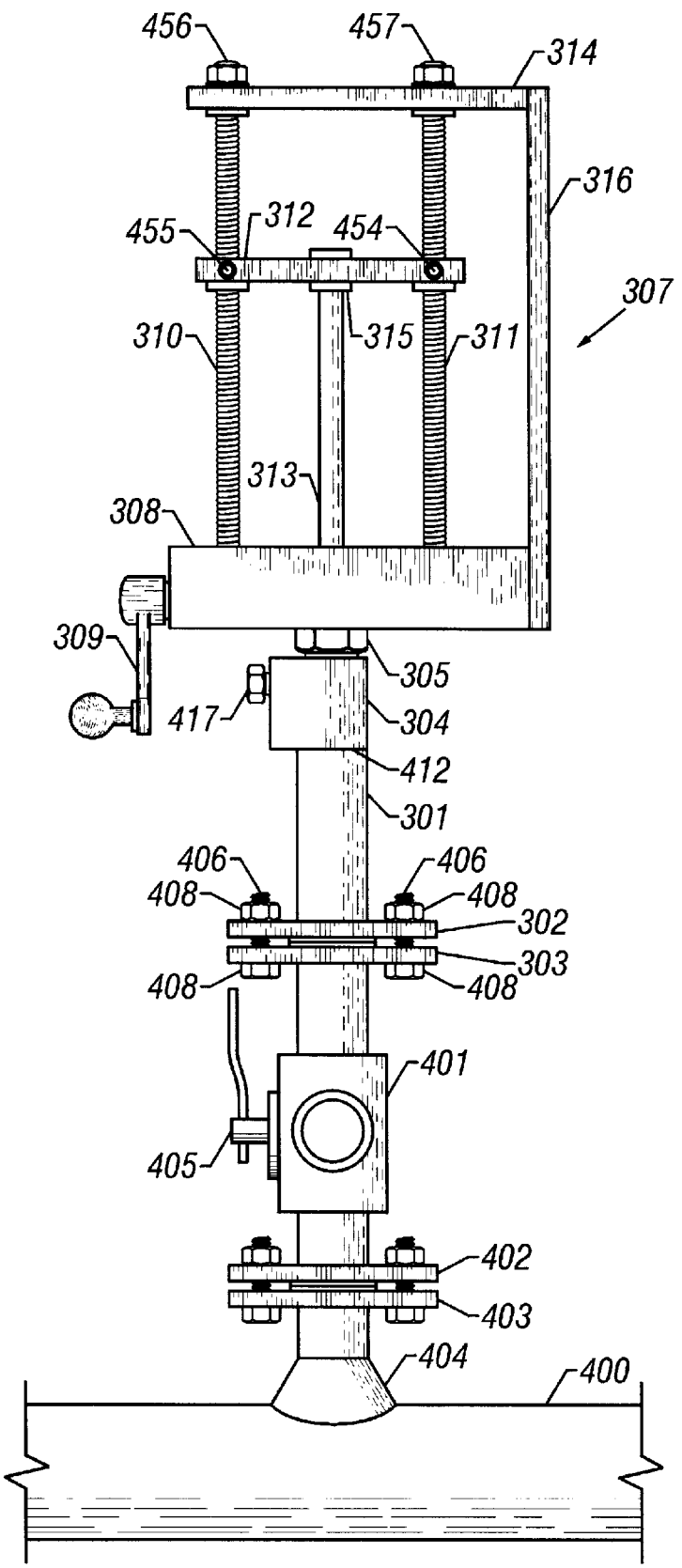

In the accompanying drawings like elements are given the same or analogous references when convenient or helpful for clarity. The same or analogous reference to these elements will be made in the body of the specification, but other names and terminology may also be employed to further explain the present invention.

DETAILED DESCRIPTION OF THE PREFERRED EMBODIMENTS AND EXEMPLARY BEST MODE FOR CARRYING OUT THE INVENTION

For a further understanding of the nature, function, and objects of the present invention, reference should now be made to the following detailed description taken in conjunction with the accompanying drawings. Detailed descriptions of the preferred embodiments are provided herein, as well as, the best mode of carrying out and employing the present invention. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure, or manner. The practice of the present invention is illustrated by the following examples which are deemed illustrative of both the process taught by the present invention and of the product and article of manufacture yielded in accordance with the present invention.

A preferred method of implementing the present invention is best illustrated by reference to the appended figures beginning with FIG. 1 which shows a test coupon holder 10. The test coupon holder 10 is shown mounted on a section of pipeline P that is to be tested by means of a pipe entry valve 12. Valve 12 is thus connected as a branch to the pipeline section P. Valve 12 is of a type which has a clear passage, such as a ball valve or plug valve, so that by a 90 degree turn applied to valve 12 by means of the operating handle 14, valve 12 can be changed from open to closed to thereby place the test coupon holder 10 either in communication with the interior of pipeline section P or isolate the holder 10 from the interior pressure within pipeline section P.

The holder 10 has an elongated housing 16 provided at one end thereof with threads 18. These threads 18 engage with the internal threads on the pipe entry valve 12 to thereby mount the test coupon holder 10 on valve 12 which in turn is threaded into an opening 20 leading to the interior of pipe section P. Housing 16 provides an internal elongated chamber 22 which in the mounted relationship shown on FIG. 1 is in alignment with the clear open passage of pipe entry valve 12 leading into the interior of pipe section P.

The end of housing 16 opposite threads 18 is provided with an end wall 24 which is conical in configuration and leads to a central aperture 26. Aperture 26 extending axially from the elongated cylindrical housing 16, has two separate diameter portions, the smaller diameter portion 28 snugly and slideably receiving a test rod 30. Rod 30 extends axially through chamber 22 of housing 16 and as shown in section in FIG. 1, with pipe entry valve 12 open, the rod projects through the valve and down into the interior of the pipe section P. The end of rod 30 has a safety stop element 32 fixedly secured thereto as by having the rod end threaded and element 32 having a female threaded portion (not shown) threaded onto the end of rod 30.

Safety stop element 32 has a generally conical portion 34 leading to its connection with rod 30. The element 32 is provided with a hollow cylindrical metallic casing 36. This casing 36 is filled with an insulating material 38 such as a phenolic material. The insulating material 38 is centrally drilled and tapped. This tapped bore in the insulating material forms the holder for the holder for the coupon C, the coupon simply being threaded at one end and screwed into the threaded bore within insulating material 38. This construction for the stop element 32 assures that the hollow metallic casing 36 protects the insulating material 38 whereas the coupon is positioned to extend freely away from the end of element 32 and rod 30. Insulating coupon C, isolated from the other metal parts of holder 10, valve 12 and pipe section P, avoids undesired electrolytic action involving coupon C.

The upper end of housing 16 above end wall 24, aperture 26, and small aperture portion 28 is threaded to receive a guide body 40 which is threaded onto the end of housing 16. A pair of annular seals 42 which may be of Teflon are disposed between the threadably engaged portions of housing 16 and guide body 40. These annular seals 42 surround the rod 30 after the rod passes through the small aperture portion 28 in the end wall 24 of housing 16. A set screw 44 is shown in FIG. 1 as threaded into a bore in guide body 40 to fixedly secure the body 40 onto the end of housing 16 securely clamping the seals 42 between body 40 and housing 16.

The guide body 40 guidingly and sealingly receives the rod 30 within a bore 50 extending through guide body 40. Intermediate the ends of bore 50 there is provided a cavity which houses a split collet 52 with the two haves of the split collet, 52 being disposed on opposite sides of the bore 50, respectively.

A threaded bore 54 leading to the cavity that houses the split collet 52 contains a locking screw 56. Thus, when locking screw 56 is threaded into bore 54 until it engages with one half of the split collet 52, pressing that half against the opposite half of the collet, the rod 30 becomes firmly clamped with respect to the guide body 40 by the split collet 52 so it is unable to be expelled from the test coupon holder 10 under pipeline pressure within the pipe section P, this same pressure existing within the chamber 22 of housing 16 when the pipe entry valve 12 is open.

By backing off on the locking screw 56, the split collet 52 releases its clamping relationship on rod 30 such that the rod may be withdrawn. Also, the release of the split collet 52 by unscrewing locking screw 56 enables the axial position of the rod 30 and therefore the location of the coupon C within the pipe section P to be adjusted. Then the split collet 52 may be reclamped by tightening down on the locking screw 56. This capability for the test coupon holder 10 is advantageous in that it enables locating the coupon C at the desired position within the pipe section P enabling the coupon holder 10 to be employed with pipelines of different diameters. Thus, the clamping means provided by the split collet 52 and locking screw 56 provides the coupon holder 10 with added versatility with respect to the areas of use.

The upper end of guide body 40 surrounding bore 50 is externally threaded at 60. In the installation shown in FIG. 1 where the coupon holder 10 is operatively associated with the open pipe entry valve 12 and pipe section P to specifically locate the coupon C in the pipe section, the length of rod 30 is such that the upper enlarged end of rod 30 is located down against the upper end of guide body 40 where bore 50 ends. In this condition, while the coupon is undergoing testing with respect to the corrosive conditions within the pipe section P, as those corrosive conditions as experienced within the fluid material flow through the pipe, an internally threaded cap 62 may be threaded onto threads 60 on guide body 40. This cap 62 acts to positively hold the rod 30 and coupon C in the desired predetermined position during the time period that the coupon C is being exposed to testing the corrosive conditions.

When the time period for the corrosive conditions test has been completed, the operator need merely remove the cap 62, threading it off of threads 60 of body 40. The presence of cap 62 avoids any danger of rod 30 being expelled from the coupon holder 10 by pressure existing within chamber 22 of housing 16. This feature becomes particularly important should someone tamper with and thereby release the split collet 52 by unscrewing locking screw 56. Such a release of split collet 52 to free rod 30 without the presence of cap 62 could result in rod 30 being rapidly at expelled from the coupon holder under the pipeline pressure.

It should also be pointed out that the construction of safety stop element 32 affixed to the end of rod 30 offers the coupon holder 10 added safety should cap 62 not be present and the split collet 52 become released. In such event, while the rod 30 would be rapidly expelled from the holder 10 under the pipeline pressure, the rod 30 would not be totally ejected from the coupon holder 10. Instead, the conical portion 34 of safety stop element 32 would pass through chamber 22 in housing 16 and engage against the apertured end wall 24 of housing 16 thereby preventing further expulsion of rod 30 with cap 62 removed and split collet 52 released.

The elongated cylindrical housing 16 is provided with a passageway 64 leading from aperture 26 which communicates with chamber 22 to the exterior of housing 16. The outer portion of passageway 64 is internally threaded and a bleeder valve 70 is then threaded into passageway 64. This bleeder valve may be of conventional construction. Bleeder valve 70 enables the pressure in chamber 22 of housing 16 to be relieved when the operation of removing coupon C following termination of the corrosive testing to be carried out. A typical type bleeder valve 70 would act to close off passageway 64 when the cap portion on the valve is threaded down onto the base portion and open passageway 64 when this cap portion is unscrewed to open the bleeder valve passage.

As has been previously explained, the test coupon holder 10 is shown in FIG. 1 in its operative position relative to pipe entry valve 12 and pipe section P while the coupon C is undertaking the corrosive testing process. In contrast, FIG. 2 shows the coupon holder 10 in the condition where the coupon C is either in readiness to be introduced into the pipe section P or has been retrieved from the pipe section P following undergoing the corrosive testing of the fluid within pipe section P.

The operation undertaken in removing the coupon C from the condition of the test coupon holder 10 shown in FIG. 1 following completion of a corrosive test may be described as follows: Initially cap 62 is removed thereby exposing the upper end of rod 30 on the exterior of guide body 40. Then an override housing 80 which has an internally threaded end is threaded onto the threads 60 on the outer end of guide body 40. The override housing 80 carries a retrieving rod 82.

This retrieving rod carries a coupling 84 which mates with the upper end 86 of rod 30. This may be a threaded coupling between elements 84 and 86, a pin connection, or other suitable interconnection made between the rod 30 and the retrieving rod 82. Such connection forms no part of the invention herein.

The override housing 80 also carries a retrieving rod bushing 88 at its upper end which acts as a guide for the retrieving rod 82. The retrieving rod 82 has a handle 90 fixed to the outer end of the retrieving rod, this handle enabling the operator to manipulate rod 30 in carrying out the insertion and removal of coupon C from the interior of the pipeline section P.

Initially, in commencing to remove the coupon C from the pipeline section P after a corrosive test period has been concluded, the split collet 52 is released by unscrewing locking screw 56. This unclamps rod 30 with respect to guide body 40 and enables withdrawal of rod 30 carrying the test coupon C. However, careful control of releasing the split collet clamp 52 needs to be observed since the pipeline pressure acting on rod 30 tends to force the rod out of the coupon holder requiring control of this expelling action by firmly holding the handle 90 on the retrieving rod 82 which is coupled to rod 30.

With the retrieving rod 82 in place along with override housing 80, rod 30 is withdrawn thereby removing coupon C from within the pipe section P until it is disposed within chamber 22 of housing 16 as shown in FIG. 2.

Once the coupon C and safety stop element 32 on rod 30 have been withdrawn into the chamber 22 of housing 16, the pipe entry valve 12 is manipulated to its closed position thereby isolating the test coupon holder 10 from the pressure within the pipeline section P. With the pipe line pressure existing within chamber 22, the bleeder valve 70 which has been in a closed position will be opened thereby bleeding the pressure from within chamber 22 through passageway 64 to the exterior.

Once the pressure within chamber 22 has been relieved, the entire test coupon holder 10 starting with housing 16 may be unthreaded where the threads 18 have been threaded into the body of pipe entry valve 12. With the coupon holder 10 now separated from pipe entry valve 12, the rod 30 may be manipulated as needed to expose the coupon C still carried by the safety stop element 32. Such exposure now occurs through the open end of chamber 22 in housing 16 where it has been disconnected from the pipe entry valve 12. Necessary inspection of the coupon C upon its removal from safety stop element 32 will now be carried out in determining the corrosive conditions existing within pipeline section P.

Inserting a fresh coupon C for carrying out a further corrosive condition test essentially involves the reverse of the above described procedures. A new coupon C will be threaded into the insulator material 38 within the hollow metallic casing 36 of safety stop element 32 with this fresh coupon then being drawn up on rod 30 into the chamber 22 of housing 16. In this position such as shown on FIG. 2, the test coupon holder is in readiness to be installed upon pipe entry valve leading the interior of pipeline section P.

The bleeder valve 70 is closed and the threads 18 on housing 16 engaged with the internal threads of the pipe entry valve 12. At this stage the valve 12 is opened by manipulating handle 14 admitting the pipeline pressure into chamber 22 of housing 16 in the coupon holder 10. By reintroducing rod 30 down through chamber 22 and pipe entry valve 12, the new coupon C is introduced into the interior of pipeline section P. When rod 30 has been inserted to the desired extent to position coupon C at a predetermined position within pipeline section P, the split collet 52 is tightened by screwing in locking screw 56 until the rod 30 is firmly clamped within the guide body 40 against possible displacing forces acting on the rod and coupon by reason of the pressure within the pipeline section P which pressure now exists within chamber 22 by reason of open pipe entry valve 12.

FIG. 3 depicts an overall elevational view of one embodiment of the present invention as mounted on the pipeline 400. As shown, the pipeline 400 includes a saddle 404 welded in place which includes flange member 403. A full port valve 401, such as a ball valve, is mounted by flange member 402 to pipeline flange 403. A guide body 301 for stinger 313 is likewise mounted by a flange 302 to outer valve flange 303. A packer joint 304 is threadedly secured to guide body 301.

Stinger driving mechanism, generally indicated at 307, is threadedly mounted to packer joint 304 by connection 305 on base 308. Driving mechanism 307 is shown to comprise base 308 and a frame having one or more side members 316 and top member 314. All threaded rods 310 and 311 are rotatably mounted between top frame member 314 and base 308. Cross bar 312 is in threaded engagement with each of the threaded rods 310 and 311. In the base 308, there is a power transmission assembly which rotates all threaded rods 310 and 311 in response to rotation of crank 309. The stinger 313 is in threaded engaged to cross bar 312 by connection 315 such that when the crank 309 is rotated, stinger 313 is made to move in and out through packer joint 304, guide body 301, and valve 401 into pipeline 400.

The stinger 313 may be any of a variety of instruments or tools that requires insertion into a pipeline or vessel such as a corrosion coupon holder, sampling tube or injection device. The flanged connections shown may be easily replaced by standard threaded connections or vice versa.

Figure 4:
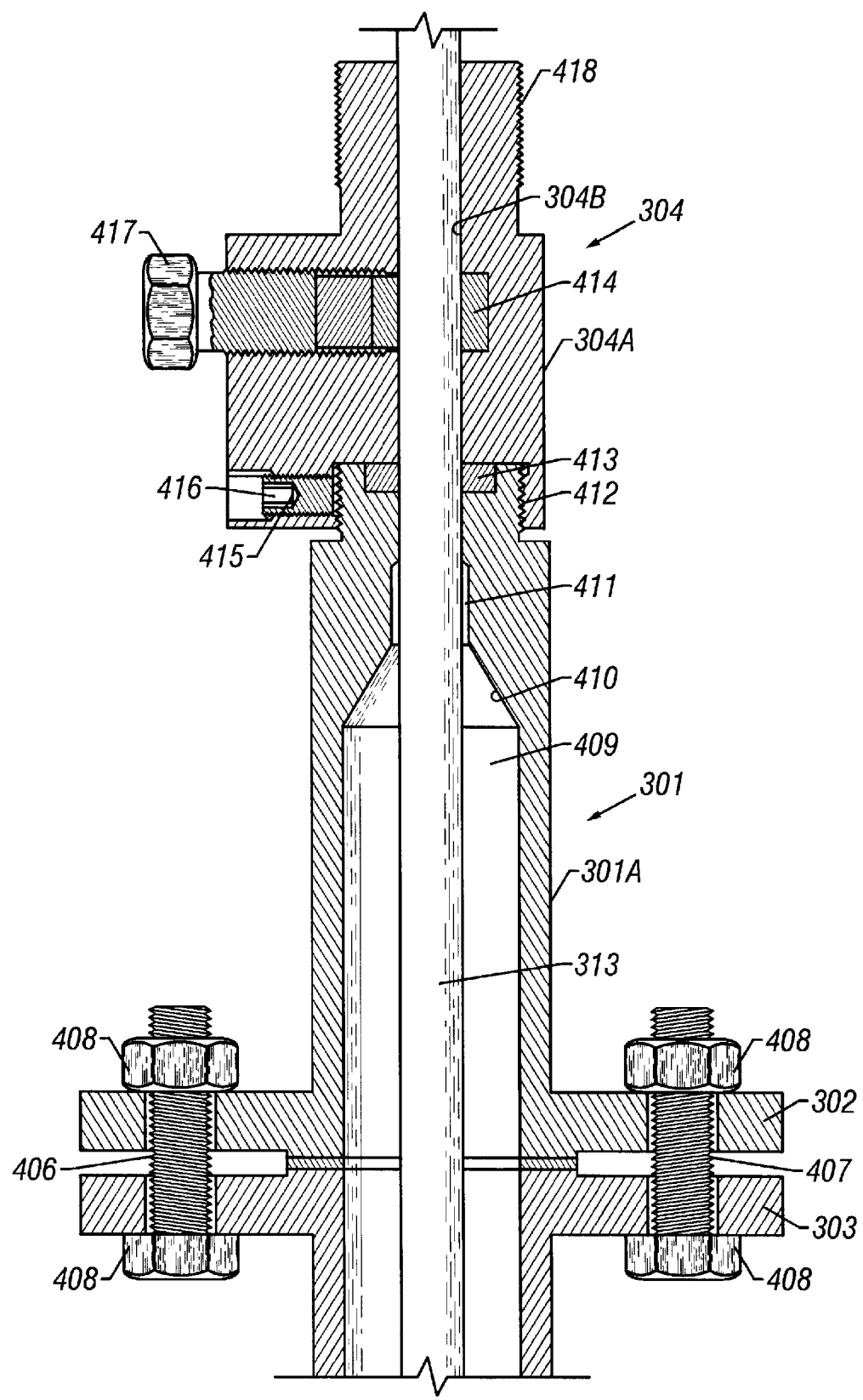

Referring now to FIG. 4, a detailed view of one embodiment of the packer joint 304 is shown mounted by internal threads 412 onto guide body 301. As noted in connection with FIG. 3, guide body 301 is mounted by flange member 302 to outer valve flange member 303. The guide body 301 includes an elongated housing 301 A which provides an internal elongated chamber 409 which is in alignment with the passage through valve 401. The upper end of housing chamber 409 ends in a conical dome 410 which leads to central aperture 411 which snugly receives stinger 313. The domed shape of the upper end of chamber 409 is designed as a safety stop. At the top of the guide body 301 is a packing seal 413 which fits about stinger 313 and is forced into tight sealing engagement therewith when packer joint 304 is threaded onto body threads 412.

Packer joint 304 is shown to comprise body 304A with an internal bore 304B there through which is in axial alignment with aperture 411 and housing chamber 409. A locking screw in the form of an Allen bolt 415 is provided to secure the seal 413 against stinger 313. A collet clamp 414 is provided to lock the stinger 313 at the desired position when collet bolt 417 engages against collet 414.

Figure 5:
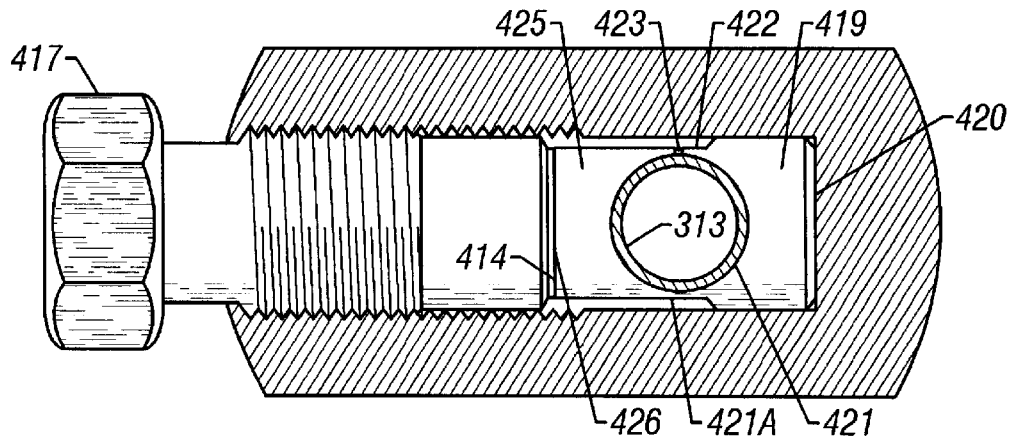
Figure 6:
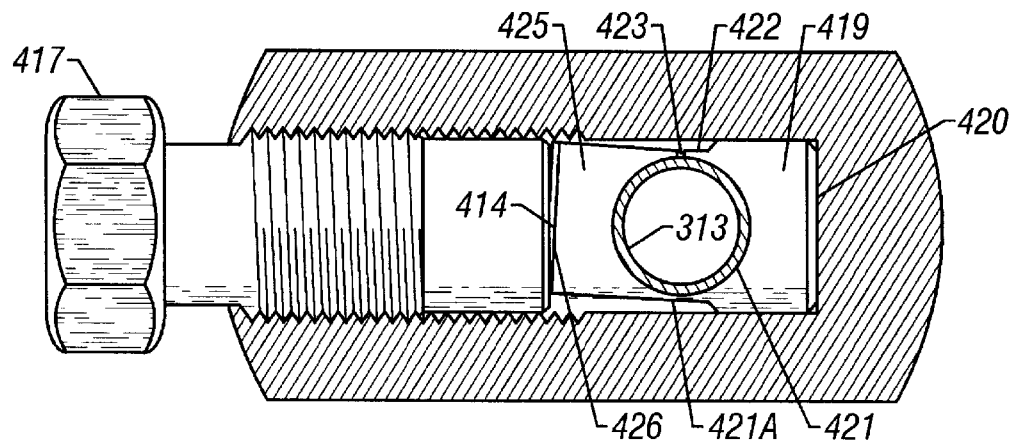
Figure 7:
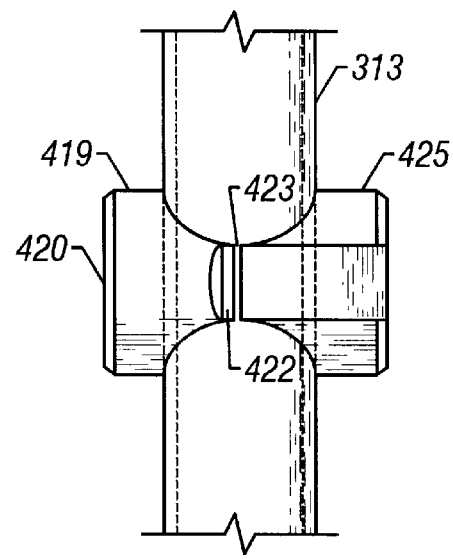

Referring now to FIGS. 5, 6, and 7, one embodiment of the collet clamp 414 is shown in detail. The collet clamp depicted therein is particularly usefull for clamping tubing such as might comprise the stinger herein because it will securely grip the tubing without collapsing the tubing. FIG. 5 shows the collet 414 as viewed from the top. The collet clamp 414 includes two top surfaces 419 and 425 connected by a saddle-shaped section 421A. Aperture 421 is adapted to fit closely around the desired stinger 313. On one side of the saddle, a split 423 is provided for resiliency. Surface 424 provides a drive area adjacent the split 423. The collet clamp 414 is mounted within packerjoint 304 such that drive area 424 is facing the collet bolt 317. When the bolt 417 engages the surface 424, reduced shoulder 422 collapses about the stinger as shown in FIG. 6 to secure the stinger in position. The gripping force is thus distributed 180 degrees about the tubing preventing deformation which could cause leakage through the packing gland. These features are shown further in the side view of FIG. 7.

While these are some of the preferred embodiments of the collet clamp, as discussed herein, many other embodiments are possible including a simple bolt or screw which would pinch or hold the stinger in place by abutment therewith.

Figure 8:
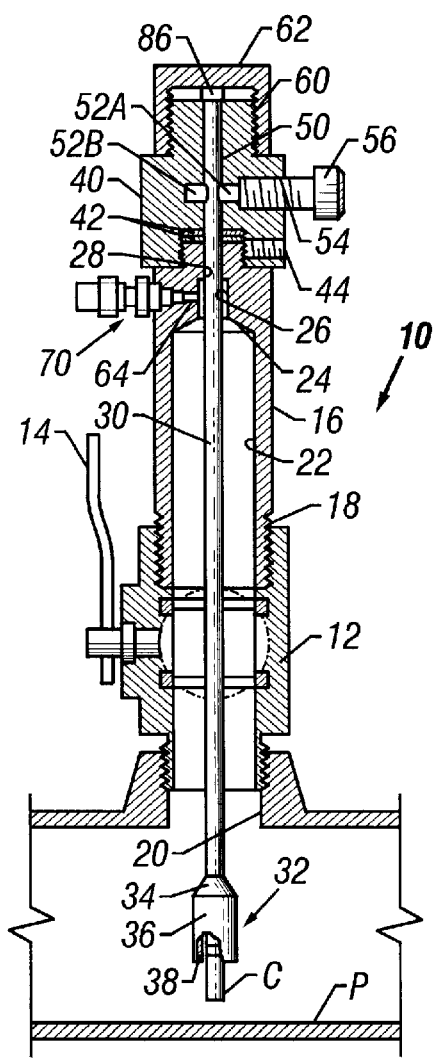
Figure 9:
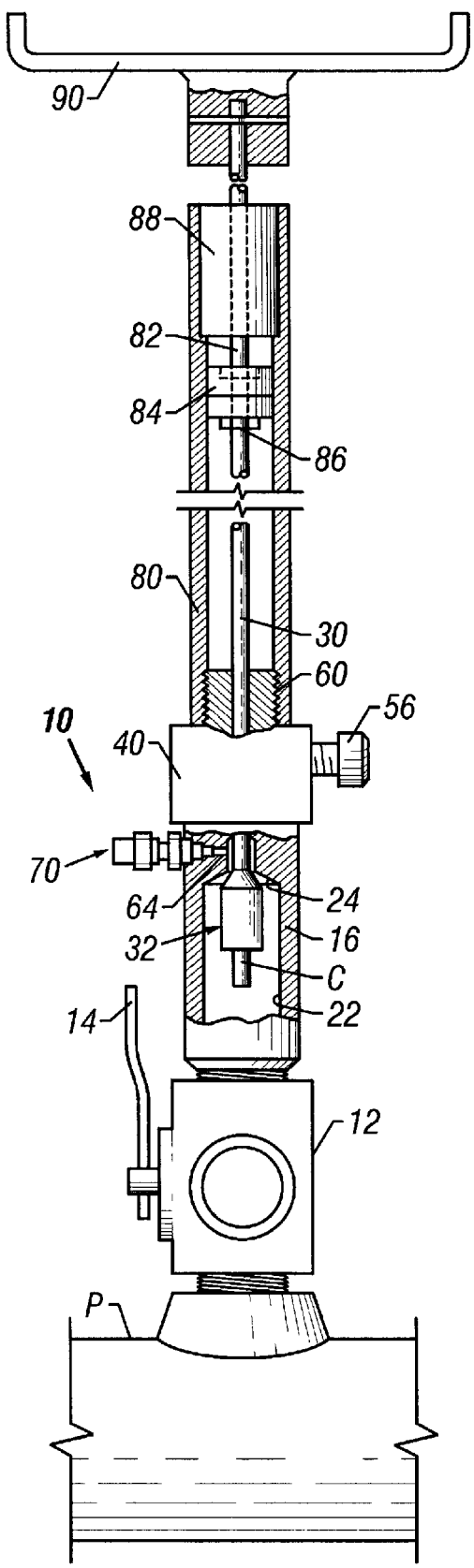

FIGS. 8 and 9 are substantially the same as FIGS. 1 and 2 and are numbered in the same way. They are presented here to draw attention to certain improvements.

It has been our experience that when two like metals are used in rod 30 and guide body 40, even when the metal is of high quality such as 316 stainless steel, the process of extraction of the rod often led to gaulding causing scratching of the rod 30 or the body 40 or both. Most frequently this damage was caused by gaulding and compression of split collet 52 B. As used herein gaulding refers to any of a variety of related processes which share the apparent catastrophic start in which one of the metals becomes hung up on the other as though a part had been caught in a hole or pit in the material leading to a variety of damages such as jerking, scratching, gouging, nicking, compressing, deforming, marring, and the like. When this compression and gaulding takes place it frequently will cause the rod 30 to freeze up so the rod can not be removed or it will cause damage and scratching of the rod 30 or the guide body 40 or both often with the creation of added damage to the seal of the unit causing leakage and failure.

Frequently this failure will arise from the over tightening of the locking bolt 56, which happens frequently in the field. This over tightening causes the locking collet 52B to be extruded and pushed back into the body 40. When this happens you lose the effect of the collet 52 and it makes no or ineffective contact with the rod 30. This sequence can lead to the rod 30 making contact with the body 40 causing further gaulding of the rod 30 and the body 40.

Unexpectedly it has been discovered that this problem can be corrected by installing or pressing a brass bushing 11A in body 40 to be the contact surface of the 316 stainless steel rod 30. (See 11A of FIG. 11 for such an installation of a brass bushing.) Alternatively, the entire guide body 40 may be formed of brass for contact with a stainless steel rod 30 as shown in FIGS. 6 and 9. In principle, it is believed that the use of dissimilar metal is the underlying factor leading to the solution to this problem. Regardless of the underlying theory it has been found that the use of a brass bushing or body effectively solves the problem.

Figure 10:
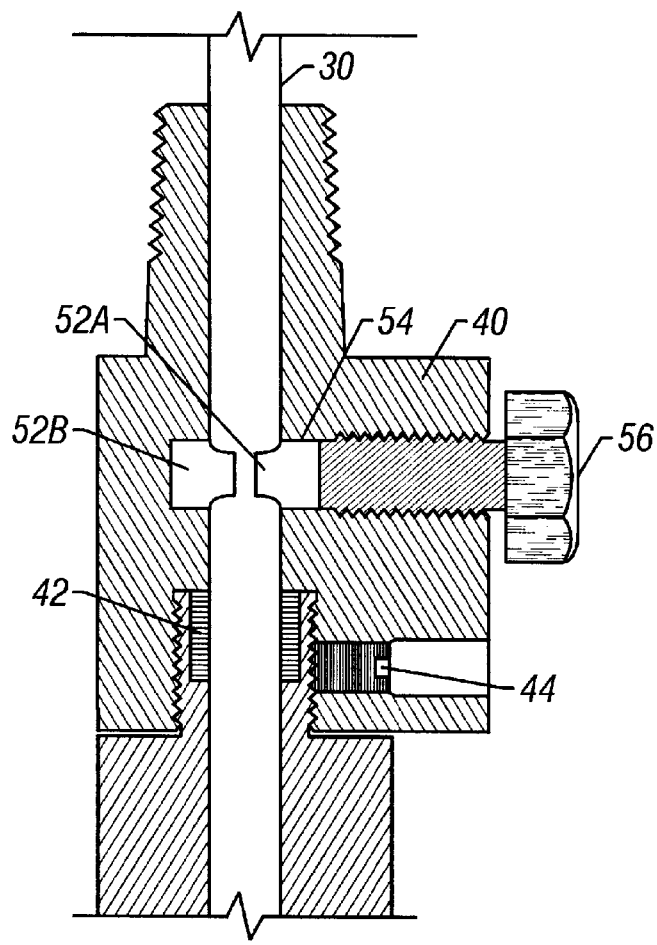

As shown in FIG. 10 the body may be made of brass. In addition to the solution provided by the use of a metal dissimilar to 316 stainless steel rod 30, when personnel in the field over tighten the locking bolt 56, it can cause collet 52 to be compressed and at least partially extruded into bore 54. Further, in the usual case having threads in the bore 54 when the collet 52A is compressed can cause the collet 52 to become locked against the rod 30. When this happens, the rod may be locked in place and its removal can be very difficult. In some cases the customer may have to shut down the pipeline to remove a coupon C from the coupon holder at the end of rod 30. Such a problem causes great expense, loss of time and production, and various other problems up and down the transmission line.

Figure 11:
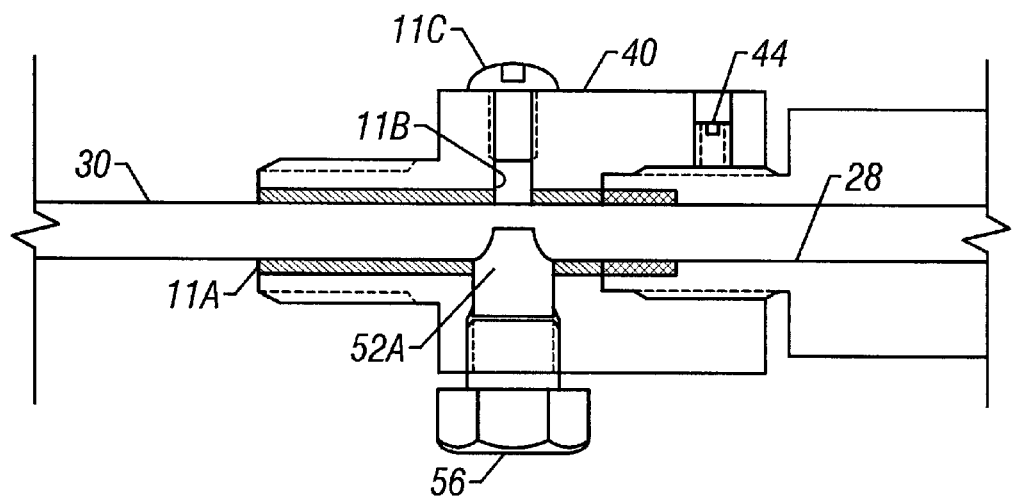

Referring now to FIG. 11, it has been found that by drilling and tapping a bore hole 11B as shown in FIG. 11 on the opposite side of the locking bolt 56 and collet 52A a bore hole 11B may be formed and capped by screw 11C.

When a jam takes place, screw 11C may be removed and a ¼" brass rod may be inserted. The brass rod (not shown) may be tapped to tap the collet 52A back freeing up the rod 30 so that it may be removed without the necessity of shutting down the pipeline.

Also shown in FIG. 11 is the embodiment of the present invention in which a brass bushing 11A is pressed within the guide body 40 to prevent the gaulding of the rod 30 or body 40.

It should be noted that while the present embodiment has been described as employing a stainless steel rod and a brass bushing or body, other materials of suitable relative hardness, tensile strength and coefficients of friction may be employed.

In summary, the present invention is directed to an apparatus for inserting and removing a stinger in the interior of a pipeline or vessel, where the stinger has an external end and an internal end. A packer assembly for sealable connection to an opening on said pipeline or vessel and adapted for sealing engagement to the stinger is provided. A clamping collet mounted within a guide body within the packer assembly is provided to releasably hold the stinger in the desired position after insertion. A metal surface is provided as a part of and within the guide body which is different from the metal of the stinger. The metal surface may be the interior face of the guide body or a bushing within the guide body. For example, the metal surface may be brass and the stinger may be stainless steel. A bore hole provides access to tap the collet to free the stinger, if necessary. The method of employing these improvements is also a part of the present invention.

It is noted that the embodiment described herein in detail for exemplary purposes is, of course, subject to many different variations in structure, design, application and methodology. Because many varying and different embodiments may be made within the scope of the inventive concepts herein taught, and because many modifications may be made in the embodiment herein detailed in accordance with the descriptive requirements of the law, it is to be understood that the details herein are to be interpreted as illustrative and not in a limiting sense. It will be understood in view of the instant disclosure, that numerous variations on the invention are now enabled to those skilled in the art. Many of the variations reside within the scope of the present teachings. It is not intended to limit the scope of the invention to the particular forms set forth, but on the contrary it is intended to cover such alternatives, modifications, and equivalents as may be included within the spirit and scope of the teachings of the present invention. Accordingly, the invention is to be broadly construed and is to be limited only by the spirit and scope of the claims appended hereto.

What is claimed is:

1. An apparatus for inserting and removing a stinger in an interior of a pipeline or vessel, said stinger having an external end and an internal end comprising: a packer assembly for sealable connection to an opening on said pipeline or vessel and adapted for sealing engagement to said stinger; and a clamping collet mounted within a guide body within said packer assembly to releasably hold said stinger in the desired position after insertion; wherein the improvement comprises providing a metal surface as a part of and within said guide body which is different from the metal of said stinger to inhibit instances of gaulding of the rod, compression freeze up of the rod, lock up of the rod, or the like.

2. The improvement of claim 1 wherein the metal surface is the interior face of the guide body.

3. The improvement of claim 1 wherein the metal surface is a bushing within said guide body.

4. The improvement of claim 1 wherein the metal surface is brass and the stinger is stainless steel.

5. The improvement of claim 1 wherein a borehole provides access to tap said collet free.

6. An apparatus for inserting and removing a stinger in an interior of a pipeline or vessel, said stinger having an external end and an internal end comprising: a packer assembly for sealable connection to an opening on said pipeline or vessel and adapted for sealing engagement to said stinger; and a clamping collet mounted within a guide body within said packer assembly to releasably hold said stinger in the desired position after insertion; wherein the improvement comprises: providing a metal surface as a part of and within said guide body which is different from the metal of said stinger-to inhibit instances of gaulding of the rod, compression freeze up of the rod, lock up of the rod, or the like.

7. The improvement of claim 6 wherein the metal surface is the interior face of the guide body.

8. The improvement of claim 6 wherein the metal surface is a bushing within said guide body.

9. The improvement of claim 6 wherein the metal surface is brass and the stinger is stainless steel.

10. The improvement of claim 6 wherein a bore hole provides access to tap said collet to free said stinger.

11. A packer assembly for inserting a stinger into a pipeline or vessel comprising: a guide body adapted to be mounted on a pipeline or vessel entry valve including an elongated housing and chamber within said housing in alignment with said entry valve; a packer joint mounted on the upper end of said housing in alignment with the passage through said entry valve; a packer joint mounted on the upper end of said guide body, including a packer joint body having a bore therethrough in axial alignment with said aperture and said chamber, said bore adapted to fit around said stinger, a collet clamp mounted within said packer joint body and adapted to fit snugly about said stinger, a collet clamp actuation means for securely but releasably tightening said collet clamp about said stinger; wherein the improvement comprises: providing a metal surface as a part of and within said guide body which is different from the metal of said stinger to inhibit instances of gaulding of the rod, compression freeze up of the rod, lock up of the rod, or the like.

12. The improvement of claim 11 wherein the metal surface is the interior face of the guide body.

13. The improvement of claim 11 wherein the metal surface is a bushing within said guide body.

14. The improvement of claim 11 wherein the metal surface is brass and the stinger is stainless steel.

15. The improvement of Claim 11 wherein a bore hole provides access to tap said collet to free said stinger.

16. An insertion apparatus for inserting and removing a stinger through a packer assembly on a pipeline or vessel, said stinger having an external end and an internal end, comprising an elongated housing defining a chamber, said housing having connecting means at one end for connecting said housing to an entry valve on said pipeline or vessel; a guide body mounted on the other end of said housing having a bore in communication with said housing; a rod received in said bore; collet means positioned and arranged within said bore of said guide body to clamp said rod; wherein the improvement comprises: providing a metal surface as a part of and within said guide body which is different from the metal of said rod-to inhibit instances of gaulding of the rod, compression freeze up of the rod, lock up of the rod, or the like.

17. The improvement of claim 16 wherein the metal surface is the interior face of the guide body.

18. The improvement of claim 16 wherein the metal surface is a bushing within said guide body.

19. The improvement of claim 16 wherein the metal surface is brass and the rod is stainless steel.

20. The improvement of claim 16 wherein a bore hole provides access to tap said collet to free said rod.

21. An approval method of preventing lock-up or damage to the apparatus of claim 16 by making the guide body of a metal different from that of the rod.

22. The method of claim 21 wherein the metal surface is that of a bushing within said guide body.

23. The method of claim 21 wherein the metal surface is brass and the rod is stainless steel.

24. The method of claim 21 wherein the collet may be tapped by means of a bore hole to free said rod.

* * * * *